US007282515B2

(12) United States Patent
Meese et al.

(10) Patent No.: US 7,282,515 B2
(45) Date of Patent: Oct. 16, 2007

(54) DERIVATIVES OF AZASPIRO COMPOUNDS FOR THE TREATMENT OF PAIN

(75) Inventors: Claus Meese, Monheim (DE); Norma Selve, Troisdorf (DE); Dirk Schmidt, Düsseldorf (DE)

(73) Assignee: Schwarz Pharma AG, Rhein (DE)

( * ) Notice: Subject to any disclaimer, the term of this patent is extended or adjusted under 35 U.S.C. 154(b) by 0 days.

(21) Appl. No.: 10/935,794

(22) Filed: Sep. 7, 2004

(65) Prior Publication Data

US 2005/0119319 A1 Jun. 2, 2005

Related U.S. Application Data

(63) Continuation of application No. PCT/EP03/01985, filed on Feb. 27, 2003.

(30) Foreign Application Priority Data

Mar. 7, 2002 (DE) ................................ 102 10 195

(51) Int. Cl.
*A61K 31/4166* (2006.01)
*A61K 31/421* (2006.01)
*A61K 31/426* (2006.01)

(52) U.S. Cl. ....................... 514/371; 514/376; 514/392

(58) Field of Classification Search ................ 514/371, 514/376, 392
See application file for complete search history.

(56) References Cited

U.S. PATENT DOCUMENTS

| | | | | |
|---|---|---|---|---|
| 2,716,648 | A | 8/1955 | Jules et al. | |
| 2,732,380 | A | 1/1956 | Reppe et al. | |
| 2,866,734 | A | 12/1958 | Shapiro et al. | |
| 3,629,276 | A | 12/1971 | Harnden | |
| 4,105,774 | A | 8/1978 | Driscoll et al. | |
| 5,132,451 | A | 7/1992 | Jennings et al. | |
| 5,319,135 | A | 6/1994 | Jennings et al. | |
| 5,393,750 | A | 2/1995 | James et al. | |
| 5,534,520 | A * | 7/1996 | Fisher et al. | 514/278 |
| 5,852,029 | A | 12/1998 | Fisher et al. | |
| 5,925,672 | A * | 7/1999 | Piomelli et al. | 514/460 |
| 5,948,807 | A | 9/1999 | Efange et al. | |

FOREIGN PATENT DOCUMENTS

| | | |
|---|---|---|
| EP | 0 017 379 | 10/1980 |
| EP | 0 021 704 | 1/1981 |
| EP | 0 028 485 | 5/1981 |
| EP | 0 008 229 | 2/1982 |
| EP | 0 116 347 | 8/1984 |
| EP | 0 249 328 | 12/1987 |
| EP | 0 252 713 | 1/1988 |
| EP | 0 269 355 B1 | 6/1988 |
| EP | 0 306 251 | 3/1989 |
| EP | 0 409 617 A2 | 1/1991 |
| EP | 0 711 292 B1 | 5/1996 |
| EP | 0 894 497 A1 | 2/1999 |
| GB | 967 718 A | 8/1964 |
| GB | 995864 | 6/1965 |
| GB | 1015026 | 12/1965 |
| WO | WO-95/03303 | 2/1995 |
| WO | WO-95/18112 | 7/1995 |
| WO | WO-99/25683 | 5/1999 |
| WO | WO-99/45975 | 9/1999 |
| WO | WO-99/61424 | 12/1999 |

OTHER PUBLICATIONS

Hamad et al., "Synthesis and biological activity of 2-thiono-[1H]-5-Spirocyclohexylimidazo[4,3-b] quinazolone and 8-azaquinazolone derivatives," Boll. Chim. Farmac Annoc, 140(4), pp. 233-237 (2001).*

Naydenova et al., II Farmaco, 57:189-194 (2002).

Sarges et al., J. Med. Chem., 31;230-243 (1988).

Hamad et al., Boll. Chim. Farmac., 140(4):233-237 (2001).

Robbe et al., Eur. J. Med. Chem.—Chim. Ther., 17(3):235-243 (1982).

Ismail et al., Egypt. J. Pharm. Sci., 40(1):79-82 (1999).

Hamad et al., Boll. Chim. Farmac.—Anno, 140(4):233-237 (2001).

Robbe et al., Eur. J. Med. Chem—Chim. Ther., 17(3):235-243 (1982).

Courtoison et al., II Farmaco—Ed. Sc., 43(2):153-160 (1987).

Sarges et al., J. Med. Chem., 31:230-243 (1988).

Scholl et al., Structural Chemistry, 10(5):355-366 (1999).

Oldfield et al., Cycloalkanespiro-5'-Hydantoins, "The Chemistry and Pharmacology of a Series of Cycloalkanespiro-5'-hydantoins", vol. 8, pp. 239-249 (1965).

Rice et al., J. Med. Chem, 6:388-405 (1963).

Grogan et al., J. Med. Chem. 8:62-73 (1965).

Lespagnol et al., Annales Pharmaceutiques Francaises, 10:15-36 (1951).

Ulbricht, Pharmazie, 42(9):598-601 (1987).

Harnden et al., J. Med. Chem., 13(2):305-308 (1970).

Newman et al., J. Am. Ch. Soc., 73:4199-4204 (1951).

Granger et al., Trav. Soc. Pharm. Montpellier, 24:244 (1964).

Regnier et al., Chimie Therapeutique, 3:174-184 (1969).

Badger et al., "Antiarthritic and Suppressor Cell Inducing Activity of Azaspiranes: Structure-Function Relationships of a Novel Class of Immunomodulatory Agents", J. Med. Chem., Am. Chem. Soc., vol. 33, No. 11, Nov. 1, 1990, pp. 2963-2970.

(Continued)

*Primary Examiner*—Rebecca Anderson
*Assistant Examiner*—Michael Barker
(74) *Attorney, Agent, or Firm*—Edwards Angell Palmer & Dodge LLP; Peter F. Corless, Esq.; Jeffrey D. Hsi, Esq.

(57) ABSTRACT

This invention relates to azaspiro compounds and their use as medications especially for the treatment of chronic, chronic-phlogistic and/or neuropathic pain. Compounds that lend themselves particularly well to the production of analgesics include 1,3-diazaspiro[4.5]decane-2,4-dion and 1,3-diazaspiro[4.5]decane-2,4-dithion.

37 Claims, 1 Drawing Sheet

OTHER PUBLICATIONS

Figure 1:
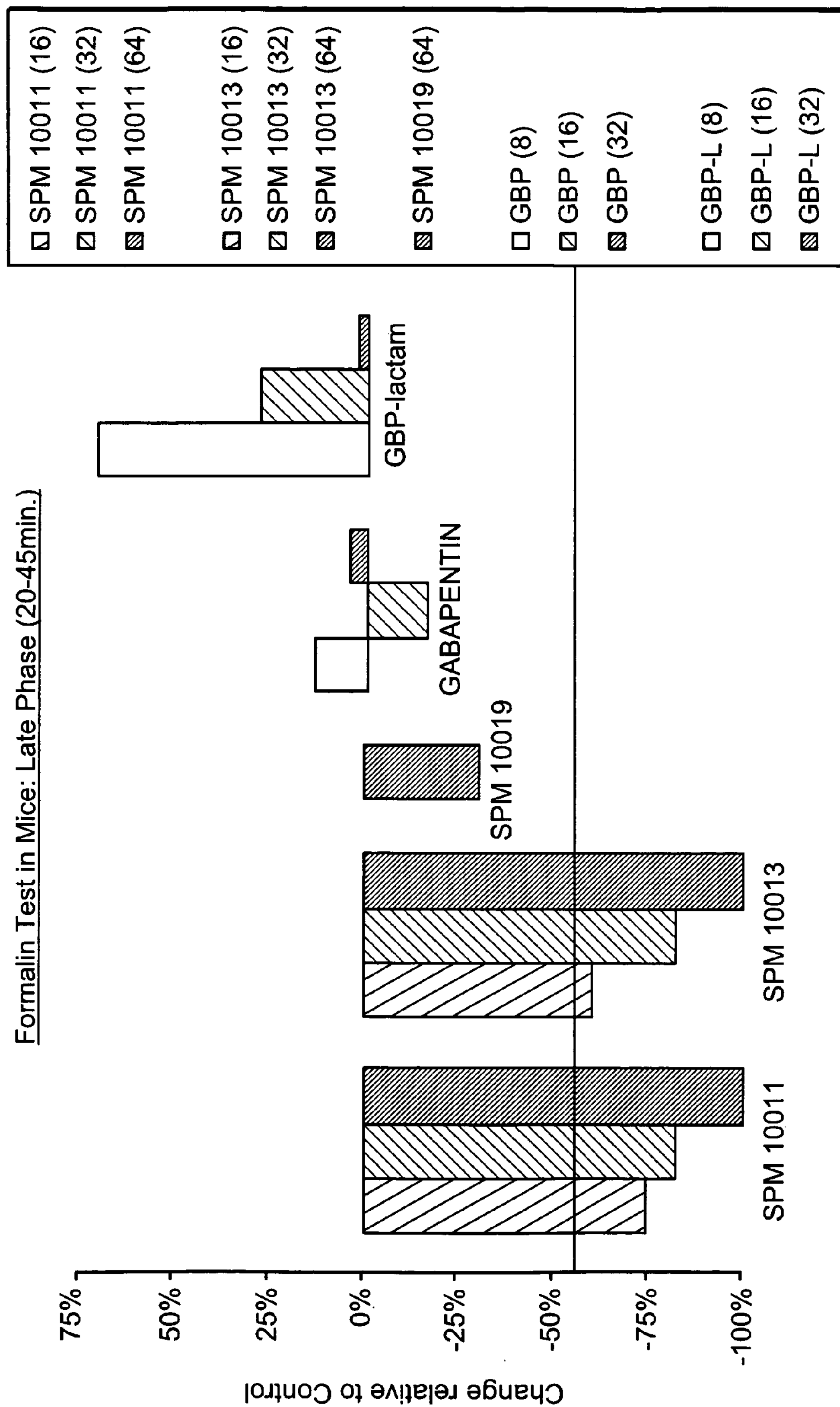

Luhndahl et al., "Synthesis and Antiviral Activities of Adamantane Spiro Compounds. 1. Adamantane and Analogous Spiro-3'-Pyrrolidines", J. Med. Chem., Am. Chem. Soc., vol. 15, No. 2, May 1, 1971, pp. 129-131.

Grogan et al., "Spiranes.IV.Alkyl,Cycloalkyl,Alkenyl,Aryl, Arylalkyl, and Hydrazono Azaspirane Derivatives", J. Med. Chem., Am. Chem. Soc., vol. 7, Aug. 2, 1963, pp. 78-87.

Panouse et al., "Immunomodulator structure-activity relationships:contribution of molesular modeling", accesion No. 134:110100 XP002248548 & Annales Pharmcaeutiques Fransaises (200), 58(5), 291-302.

STN search report: Panaiotova et al., Doklady Bolgarskoi Akademii Nauk, 1985, 38(5), 591-4.

* cited by examiner

DERIVATIVES OF AZASPIRO COMPOUNDS FOR THE TREATMENT OF PAIN

This application is a continuation of International Application PCT/EP03/01985, filed Feb. 27, 2003 and designated the United States, and which is incorporated herein by reference in its entirety.

Neuropathic pain is a difficult-to-treat form of chronic pain that is caused by injuries or disorders of the peripheral and/or central nervous system and does not respond well to traditional analgesics.

In recent times, given the similarities in the pathophysiology of epilepsy and neuropathic pain, neuropathic pain has increasingly been treated with anticonvulsive agents. One example of these is Gabapentin which, while having been approved as an antiepileptic for some time, has lately gained augmented significance in the treatment of neuropathic pain (Tremont-Lukats in Drugs 60, 2000, 1029; Block in "Nervenarzt" 72, 2001, 69).

Although the mode of action of gabapentin is not as yet fully understood, gabapentin's influence on the glutaminergic/GABAergic transmission and its effect on calcium channels offers a wide effective spectrum of activity that ranges from the treatment of epilepsy to neuropathic and other painful conditions such as migraine (Block in Nervenarzt 72, 2001, 69) or muscle and skeletal pain (EP 1 047 414) and all the way to the treatment of depression (EP 552 240), neurodegenerative illnesses (EP 446 570), anxiety and panic conditions (EP 804 182) or mania (EP 825 857).

One drawback of gabapentin is that, when stored, it forms toxic gabapentin-lactam (2-azaspiro[4.5]decan-3-on), and so is the associated difficulty to produce stable gabapentin formulations.

WO 99/25683 proposes a large number of pyrrolidinone compounds, substituted in position 4 and also encompassing azaspiro compounds such as gabapentin-lactam, for the treatment of diseases that are accompanied by elevated glutamate levels, for instance epilepsy, Alzheimer's, ALS or Parkinson's. An in-vitro model shows the effectiveness of gabapentin-lactam in ischemia and its reduction of the glutamate level. It also demonstrates the neuroprotective effect of gabapentin-lactam in a rat model. But because of its toxicity, gabapentin-lactam is not suitable for human therapy. Nor does WO 99/25683 give any indication to the effect that the pyrrolidones claimed are suitable for the treatment of neuropathic pain.

DE 25 57 220 describes N-substituted gabapentin-lactam derivatives for the treatment of epilepsy and cerebral disorders. There is no mention of its use as an analgesic.

Azaspiro compounds with aryl substituents for pain therapy are described in EP 337 547, EP 687 268, EP 880 528, EP 894 497, EP 906 315, EP 912 579, EP 929 554, EP 977 758 and EP 989 987. None of these documents suggests that desaryl azaspiro compounds also have analgetic potential.

EP A 116 347 proposes amino-substituted 1-azaspiro[4.5.] decanes and undecanes for the treatment of pain. It does not reveal any 2-azaspiro compounds or 1,3-diazaspiro compounds.

In clinical practice there are but few agents that have proved effective and suitable for the treatment of chronic or neuropathic pain; accordingly, for that indication there remains a great need for innovative medications.

It is therefore the objective of this invention to introduce alternative medicines for the treatment of pain and especially of chronic, chronic-phlogistic and/or neuropathic pain.

A surprising discovery has revealed that gabapentin-lactam-derived azaspiro compounds of the general formula I offer greater analgesic potency than gabapentin and gabapentin-lactam while at the same time being less toxic than gabapentin-lactam.

The azaspiro compounds according to this invention that are suitable for therapeutic application are expressed in Formula I.

Formula I

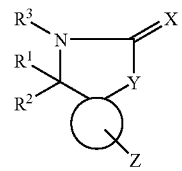

where

X and Y, independently of each other, represent S, NH or O;

$R^1$ is hydrogen and $R^2$ is selected from among hydrogen, hydroxy, formyl, carboxy, halogen, mercapto, sulfonyl, amino, amido or from a —$R^7Q^1$ group or where $R^1$ and $R^2$ jointly form an oxo- or thioxo group;

$R^3$ represents hydrogen, hydroxy, amino or a —$R^8Q^2$ group;

Z is a saturated or unsaturated ring that is connected to the first, heterocyclic ring via a joint C atom, that has 4-10 members including the azaspiro atom, that may have, in addition to carbon atoms, one or two ring-forming hetero atoms selected from O or S, and that is either unsubstituted or substituted with one or several substituents selected from among hydrogen, hydroxy, formyl, carboxy, halogen, mercapto, sulfonyl, amino, amido or a —$R^9Q^3$ group;

$R^7$, $R^8$ and $R^9$, independently from one another, represent $C_{1-5}$ alkyl, $C_3$-$C_5$ cycloalkyl, $C_{2-5}$ alkenyl, $C_{2-5}$ alkinyl, $C_{1-5}$ alkoxy, $C_{1-5}$ alkyl carbonyl, $C_{1-5}$ alkoxy carbonyl, $C_{1-5}$ alkylthio, $C_{1-5}$ alkylamino, $C_{1-5}$ alkyl sulfinyl, $C_{1-5}$ alkyl sulfonyl, $C_{1-5}$ alkylamino-$C_{1-5}$ alkyl, $C_{1-5}$ alkylthio-$C_{1-5}$ alkyl or $C_{1-5}$ alkoxy-$C_{1-5}$ alkyl;

$Q^1$, $Q^2$ and $Q^3$, independently of one another, represent hydrogen, hydroxy, formyl, carboxy, halogen, mercapto, sulfonyl, amino or amido.

The azaspiro compounds may be in the form of a free base or of pharmaceutically acceptable salts and in either form they are an object of this invention.

Moreover, depending on substituents, the azaspiro compounds may be obtained in various tautomeric forms which, if necessary, can be stabilized through salification. These tautomers and their salts as well are an object of this invention.

Pharmaceutically acceptable salts include all biocompatible salts that largely preserve the pharmacological properties of the active ingredients without causing any undesirable toxic effects. Examples include in particular the additive salts of inorganic or organic acids such as hydrogen chloride, hydrogen bromide, acetic acid, citric acid, tartaric acid, oxalic acid, fumaric acid, malic acid, succinic acid or methane sulfonic acid.

Also, as those skilled in the art are aware, azaspiro compounds may exist in optically inactive or active form depending on the substituents. Therefore, pure enantiomers as well as racemates or optically inactive compounds are explicitly included as objects of this invention.

For the purpose of this invention, the terms used above are to be understood as follows:

In this patent application, "$C_{1-5}$ alkyl" refers to a radical of a saturated aliphatic hydrocarbon group with 1-5 C-atoms that may or may not be branched. Examples of $C_{1-5}$ alkyls include methyl, ethyl, n-propyl, iso-propyl, n-butyl, iso-butyl, s-butyl, t-butyl, n-pentyl, iso-pentyl, neopentyl, t-pentyl, 1-methylbutyl, 2-methylbutyl, 1-ethylpropyl, 1.2-dimethylpropyl.

"$C_{2-5}$ alkenyl" and "$C_{2-5}$ alkinyl" in this patent application refer to radicals with 2-5 atoms that differ from the above-defined alkyls by virtue of at least one double or triple bond.

"$C_{3-6}$ cycloalkyl" refers to a radical of the group encompassing cyclopropyl, cyclobutyl, cyclopentyl and cyclohexyl.

For the purpose of this patent application, the term "hydrocarbon ring" refers to a substituted or unsubstituted ring whose ring-forming atoms consist exclusively of carbons and which is thus free of any ring-forming heteroatoms.

The term "$C_{1-5}$ alkoxy" refers to the radical —O—$C_{1-5}$ alkyl.

The term "$C_{1-5}$ alkythio" refers to the radical —S—$C_{1-5}$ alkyl.

The term "$C_{1-5}$ alkylamino" refers to the radical —NH—$C_{1-5}$ alkyl.

The term "$C_{1-5}$ alkylsulfinyl" refers to the radical —S(O)—$C_{1-5}$ alkyl.

The term "$C_{1-5}$ alkylsulfonyl" refers to the radical —$S(O_2)$—$C_{1-5}$ alkyl.

The term "$C_{1-5}$ alkylcarbonyl" refers to the radical —C(O)—$C_{1-5}$ alkyl.

The term "$C_{1-5}$ alkoxycarbonyl" refers to the radical —C(O)—O—$C_{1-5}$ alkyl.

The term "$C_{1-5}$ alkylamino-$C_{1-5}$ alkyl" refers to the $C_{1-5}$ alkyl-NH—$C_{1-5}$ alkyl group.

The term "$C_{1-5}$ alkythio-$C_{1-5}$ alkyl" refers to the $C_{1-5}$ alkyl-S—$C_{1-5}$ alkyl group.

The term "$C_{1-5}$alkoxy-$C_{1-5}$ alkyl" refers to the $C_{1-5}$ alkyl-O—$C_{1-5}$ alkyl group.

The term "halogen" refers to a radical of the group including F, Cl, Br, I. The term "thioxo group" refers to the ═S group.

One preferred object of this invention is a compound per general formula I, used as a medication, in which the ring Z is a hydrocarbon ring. In another form of implementation of the invention, the ring Z is a ring-forming oxygen or sulfur atom.

One preferred object of this invention encompasses compounds per general formula I for medical applications, in which the ring Z including the azaspiro atom is a 5-8-member ring and, most desirably, a 5-, 6- or 7-member ring.

In another preferred form of implementation of the invention, the ring Z is an unsubstituted ring and most desirably an unsubstituted hydrocarbon ring which, including the azaspiro atom, features 5, 6 or 7 ring-forming C-atoms.

In another form of implementation of the invention, the ring Z is a 5-, 6- or 7-member hydrocarbon ring substituted with a radical that is preferably selected from among hydroxy, formyl, carboxy, halogen, mercapto, sulfonyl, amino, amido or from the —$R^9Q^3$ group, where $R^9$ is preferably a $C_{1-5}$ alkyl and $Q^3$ is preferably selected from hydrogen, hydroxy, halogen, amino or sulfonyl.

In another preferred form of implementation the ring Z is saturated and preferably constitutes a saturated hydrocarbon ring that is most desirably unsubstituted.

In a particularly preferred form of implementation of the invention the ring Z consists of cyclopentane, cyclohexane or cycloheptane.

In another preferred form of implementation of the invention, both the substituents $R^1$ and $R^2$ of the compounds per formula I consist of hydrogen or together form an oxo or thioxo group.

In another preferred form of implementation of the invention the substituent $R^3$ is hydrogen.

In another preferred implementation of the invention, X is sulfur or oxygen.

Thus, a preferred form of implementation of the invention relates to azaspiro compounds per general formula I for use as medicines, where X and Y, independently of each other, are S or O;

$R^1$ is hydrogen and $R^2$ is selected from among hydrogen, hydroxy, formyl, carboxy, halogen, mercapto, sulfonyl, amino, amido or from a —$R^7Q^1$ group where $R^1$ and $R^2$ jointly form an oxo or thioxo group, with both $R^1$ and $R^2$ most desirably being hydrogen;

$R^3$ is hydrogen;

Z is a saturated or unsaturated hydrocarbon ring that is connected to the first heterocyclic ring via a common C-atom and, including the azaspiro atom, consists of 5-7 members, is free of ring-forming heteroatoms and is unsubstituted, or substituted with one or two substituents selected from among hydrogen, hydroxy, formyl, carboxy, halogen, mercapto, sulfonyl, amino, amido or a —$R^9Q^3$ group where Z is ideally saturated.

$R^7$ and $R^9$, independently of each other, are $C_{1-5}$ alkyl, $C_3$-$C_6$ cycloalkyl, $C_{2-5}$ alkenyl, $C_{2-5}$ alkinyl, $C_{1-5}$ alkoxy, $C_{1-5}$ alkylcarbonyl, $C_{1-5}$ alkoxycarbonyl, $C_{1-5}$ alkylthio, $C_{1-5}$ alkylamino, $C_{1-5}$ alkylsulfinyl, $C_{1-5}$ alkylsulfonyl, $C_{1-5}$ alkylamino-$C_{1-5}$ alkyl, $C_{1-5}$ alkylthio-$C_{1-5}$ alkyl or $C_{1-5}$ alkoxy-$C_{1-5}$ alkyl;

$Q^1$ and $Q^3$, independently of each other, are hydrogen, hydroxy, formyl, carboxy, halogen, mercapto, sulfonyl, amino or amido.

A particularly preferred form of implementation of this invention consists of azaspiro compounds per general formula I and their therapeutic use, with Y being a secondary nitrogen and $R^3$ being a hydrogen atom, with the azaspiro compound thus following the general formula I a:

Formula Ia

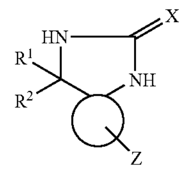

where the nature of X, $R^1$, $R^2$ and Z is as indicated above.

One preferred object of this invention encompasses azaspiro compounds per general formula Ia in which the ring Z of the azaspiro compound is an unsubstituted ring and/or a saturated ring with preferably 5, 6 or 7 ring-forming atoms including the azaspiro atom.

In a preferred implementation of the invention the ring Z of the azaspiro compound per general formula Ia is a hydrocarbon ring and most desirably a saturated and/or unsubstituted hydrocarbon ring ideally of cyclopentane, cyclohexane or cycloheptane.

In another preferred implementation of the invention the substituents $R^1$ and $R^2$ are both hydrogen or jointly form an oxo or thioxo group.

In yet another preferred implementation, X is sulfur or oxygen.

The formula Ia azaspiro compounds particularly preferred for use as medications are 1-3-diaza-spiro[4.5]decane-2.4-dion 1-3-diaza-spiro[4.5]decane-2.4-dithion 1-3-diaza-spiro[4.5]decane-2-on 1-3-diaza-spiro[4.5]decane-2-thion Another preferred implementation of the invention relates to azaspiro compounds per general formula I in which the substituent Y is an oxygen atom and $R^3$ is hydrogen. These azaspiro compounds follow the general formula I b:

Formula Ib

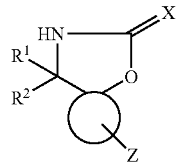

where the nature of $R^1$, $R^2$, X and Z is as indicated above.

A preferred object of this invention encompasses azaspiro compounds per general formula I b for use in medicines, in which the ring Z of the azaspiro compound is an unsubstituted ring and/or a saturated ring preferably with 5, 6 or 7 ring-forming atoms including the azaspiro atom.

In a particularly preferred implementation of the invention the ring Z of the azaspiro compound per general formula I b is a saturated and/or unsubstituted hydrocarbon ring ideally of cyclohexane.

In another preferred implementation of the invention the substituents $R^1$ and $R^2$ are both hydrogen or together form an oxo or thioxo group.

In another preferred implementation, X is sulfur or oxygen.

The particularly preferred formula I b azaspiro compounds are 1-oxa-3-aza-spiro[4.5]decane-2-on 1-oxa-3-aza-spiro[4.5]decane-2-thion Another object of this invention consists of pharmaceutical compositions encompassing an azaspiro compound per general formula I, as described above, as well as at least one pharmaceutically acceptable adjuvant.

Those skilled in the art are aware of the fact that the pharmaceutical formulation can vary as a function of the intended mode of application. Accordingly, the pharmaceutical formulation may be adapted for instance for intravenous, intramuscular, intracutaneous, subcutaneous, oral, buccal, sublingual, nasal, transdermal, inhalational, rectal or intraperitoneal administration.

Those skilled in the art of pharmaceutics are familiar with suitable pharmaceutical carrier substances and adjuvants such as fillers, diffusers, binders, lubricants, stabilizers, flavorings, antioxidants, preservatives, dispersants or solvents, buffers or electrolytes.

These substances are described in standard references for instance by Sucker, Fuchs and Speiser ("Pharmazeutische Technologie", published by Georg Thieme Verlag, Stuttgart).

In a preferred implementation of the invention, the pharmaceutical compositions containing the novel compounds are administered orally and may be provided for instance in the form of capsules, tablets, powder, granules, lozenges or liquids.

Alternative pharmaceutical preparations may be in the form for instance of solutions for infusion or injection, of oils, suppositories, aerosols, sprays, microcapsules or microparticles.

The medicine may be a quick-release formulation whenever a fast-acting drug is needed, for instance in cases of acute chronic or neuropathic pain. Corresponding formulations are described in such publications as EP 159 237 or EP 1 126 821.

If, on the other hand, protracted release is desired, a slow-acting formulation can be made available. Prior art has produced corresponding oral formulations.

The pharmaceutical formulations preferably include a compound per general formula Ia Formula Ia

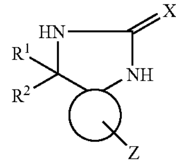

where the nature of X, $R^1$, $R^2$ and Z is as indicated above.

A preferred object of this invention consists in pharmaceutical compositions encompassing azaspiro compounds per general formula Ia in which the ring Z of the azaspiro compound is an unsubstituted ring and/or a saturated hydrocarbon ring with 5, 6 or 7 C-atoms including the azaspiro atom.

In a particularly preferred implementation of the invention the pharmaceutical formulation comprises an azaspiro compound per general formula Ia in which the ring Z consists of cyclopentane, cyclohexane or cycloheptane.

In another preferred implementation of the invention the pharmaceutical formulation encompasses an azaspiro compound per general formula Ia in which the substituents $R^1$ and $R^2$ are both hydrogen or jointly form an oxo or thioxo group.

In another particularly preferred implementation, X is oxygen or sulfur.

Especially preferred pharmaceutical compositions contain azaspiro compounds per formula Ia selected from among 1-3-diaza-spiro[4.5]decane-2.4-dion 1-3-diaza-spiro[4.5]decane-2.4-dithion 1-3-diaza-spiro[4.5]decane-2-on 1-3-diaza-spiro[4.5]decane-2-thion and their pharmaceutically acceptable salts as well as a pharmaceutically acceptable carrier substance or adjuvant.

In another form of implementation of the invention, the pharmaceutical formulation encompasses an azaspiro compound per general formula Ib as described further above. Examples of such compounds include 1-oxa-3-azaspiro[4.5]decane-2-on or 1-oxa-3-azaspiro[4.5]decane-2-thion.

Another object of this invention relates to retail packages containing at least one pharmaceutical formulation as described above as well as instructions for its use. A retail package of this type may contain other medications as well. For example, the retail package could additionally contain another analgesic, a sedative, an ergotamine derivative, an antiemetic agent, an anti-inflammatory agent or an antidepressant.

Surprisingly, in pharmacologic comparison studies the compounds according to this invention have displayed a high level of effectiveness in a formalin test, an in-vivo test for the predictability of the potential effectiveness of a substance in the treatment of chronic or chronic-phlogistic and/or neuropathic pain (Tjolsen and Herle, Handbook Exp. Pharmacol. Vol 130, Ed: Dickenson & Besson, Springer Verlag 1997, page 6).

FIG. 1 and Table 1 show the reaction of test animals 20-45 minutes after the intraperitoneal administration of selected compounds. In each case, the maximum dosage selected for the concentration of azaspiro compounds was held, by a factor of about 2, below the toxic dose previously determined in the IRWIN test (Irwin, Psychopharmacologia 13 (1968) 222).

The abbreviations used in FIG. 1 signify the following: SPM 10011 stands for 1,3-diazaspiro[4.5]decane-2,4-dion. SPM 10013 stands for 1,3-diazaspiro[4.5]decane-2,4-dithion. SPM 10019 stands for 1,3-diazaspiro[4.5]decane-2-on. GBP means gabapentine. Parenthesized in the legend behind the name of the substance is the dosage of the substance in mg/kg of body weight.

As can be seen in FIG. 1 and Table 1, the compounds per this invention surprisingly exhibited a significantly greater potency in the formalin test than gabapentin and gabapentin-lactam that were used for comparison.

Moreover, the side effects encountered with the novel compounds above the maximally tolerable dosages (sedation, tremor, hypothermia) were substantially less severe than those of GPL where a significant lethality rate was observed.

TABLE 1

| Compound | Dosage (mg/kg) | Mean deviation of the pain reaction compared to control (%) (n minutes after administration of formalin) 20–25' | 30–35' | 40–45' |
|---|---|---|---|---|
| SPM 10011 | | | | |
| Test series 1 | 64 | −100 | −100 | −80 |
| (n = 10) | 32 | −82 | −64 | −64 |
| | 16 | −75 | −11 | −55 |
| Test series 2 | 64 | −100 | −100 | −97 |
| (n = 10) | 16 | −84 | −21 | −34 |
| | 4 | −62 | (+) | ±0 |
| SPM 10013 | | | | |
| Test series 1 | 64 | −98 | −95 | −78 |
| (n = 10) | 32 | −82 | −60 | −30 |
| | 16 | −60 | −14 | −49 |
| SPM 10019 | | | | |
| (n = 10) | 32 | −52 | ±0 | −40 |
| GPL | | | | |
| Test series 2 | 32 | −64 | −15 | −46 |
| (n = 10) | 16 | −74 | −40 | −41 |
| | 8 | −58 | −18 | −15 |
| Test series 1 | 32 | (+) | −10 | n/d |
| (n = 10) | 16 | (+) | (+) | n/d |
| | 8 | (+) | (+) | n/d |
| Morphine* | 8 | −87 | −95 | −88 |

(+): Intensified pain reaction
n/d = not determined
*Average of 9 test series

It follows that the azaspiro compounds that are suitable for therapy lend themselves particularly well to the treatment of pain, especially chronic, chronic-phlogistic and/or neuropathic pain.

Accordingly, one object of this invention is the use of an azaspiro compound per general formula II

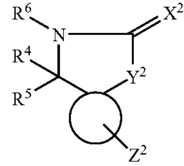

Formula II where $X^2$ and $Y^2$, independently of each other, represent S, NH or O;

$R^4$ is hydrogen and $R^5$ is selected from among hydrogen, hydroxy, formyl, carboxy, halogen, mercapto, sulfonyl, amino, amido or a —$R^{10}Q^4$ group or where $R^4$ and $R^5$ jointly form an oxo or thioxo group;

$R^6$ is hydrogen, hydroxy, amino or a —$R^{11}Q^5$ group;

$Z^2$ is a saturated or unsaturated ring that is connected to the first heterocyclic ring via a common C-atom, that consists of 4-10 members including the azaspiro atom, that may have, in addition to carbon atoms, one or two ring-forming heteroatoms selected from N, O or S, and that is unsubstituted or substituted with one or several substituents selected from among hydrogen, hydroxy, formyl, carboxy, halogen, mercapto, sulfonyl, amino, amido or a —$R^{12}Q^6$ group;

$R^{10}$, $R^{11}$ and $R^{12}$, independently of one another, represent $C_{1-5}$ alkyl, $C_3$-$C_6$ cycloalkyl, $C_{2-5}$ alkenyl, $C_{2-5}$ alkinyl, $C_{1-5}$ alkoxy, $C_{1-5}$ alkylcarbonyl, $C_{1-5}$ alkoxycarbonyl, $C_{1-5}$ alkythio, $C_{1-5}$ alkylamino, $C_{1-5}$ alkylsulfinyl, $C_{1-5}$ alkylsulfonyl, $C_{1-5}$ alkylamino-$C_{1-5}$ alkyl, $C_{1-5}$ alkylthio-$C_{1-5}$ alkyl or $C_{1-5}$ alkoxy-$C_{1-5}$ alkyl;

$Q^4$, $Q^5$ and $Q^6$, independently of one another, are hydrogen, hydroxy, formyl, carboxy, halogen, mercapto, sulfonyl, amino or amido;

as well as possible tautomers and/or pharmaceutically acceptable salts for producing a medication for the treatment of pain, especially chronic, chronic-phlogistic and/or neuropathic pain.

One preferred object of this invention is the use of a compound per general formula II in which the ring $Z^2$ is a hydrocarbon ring. In another implementation of the invention the ring $Z^2$ encompasses a ring-forming oxygen or sulfur atom.

One preferred object of the invention is the use of the compounds per general formula II in analgesics where the ring $Z^2$, including the azaspiro atom, is a 5-8-member and especially a 5-, 6- or 7-member ring.

In another preferred implementation of the invention, the ring $Z^2$ of the azaspiro compound that is used for producing the analgesic is an unsubstituted ring and desirably an unsubstituted hydrocarbon ring with 5, 6 or 7 ring-forming C-atoms including the azaspiro atom.

In another implementation of the invention, the ring $Z^2$ is a 5-, 6- or 7-member hydrocarbon ring substituted with a radical that is preferably selected from among hydroxy, formyl, carboxy, halogen, mercapto, sulfonyl, amino, amido or the —$R^{12}Q^6$ group where $R^{12}$ preferably consists of $C_{1-5}$ alkyl and $Q^6$ is preferably selected from among hydrogen, hydroxy, halogen, amino or sulfonyl.

In another preferred implementation, the ring $Z^2$ that is used for producing the azaspiro compound for the analgesics is saturated and preferably constitutes a saturated hydrocarbon ring which is ideally unsubstituted.

In a particularly preferred implementation of the invention the analgesic is produced using a formula II azaspiro compound in which the ring $Z^2$ is cyclopentane, cyclohexane or cycloheptane.

In another preferred implementation of the invention the substituents $R^4$ and $R^5$ of the formula II compounds are both hydrogen or jointly form an oxo or thioxo group.

In another preferred implementation of the invention the substituent $R^6$ is hydrogen.

In yet another preferred implementation of the invention, $X^2$ is sulfur or oxygen.

In another preferred implementation of the invention the analgesic is produced using a compound per general formula II, where $X^2$ and $Y^2$, independently of each other, are S or O;

$R^4$ is hydrogen and $R^5$ is selected from among hydrogen, hydroxy, formyl, carboxy, halogen, mercapto, sulfonyl, amino, amido or a —$R^{10}Q^4$ group or where $R^4$ and $R^5$ jointly form an oxo or thioxo group, and where, most preferably, both $R^4$ and $R^5$ are hydrogen;

$R^6$ is hydrogen;

$Z^2$ is a saturated or unsaturated hydrocarbon ring that connects to the first heterocyclic ring via a common C-atom, that has 5-7 members including the azaspiro atom, that is free of ring-forming heteroatoms and that is unsubstituted or is substituted with one or two substituents selected from among hydrogen, hydroxy, formyl, carboxy, halogen, mercapto, sulfonyl, amino, amido or a —$R^{12}Q^6$ group, with $Z^2$ most desirably being saturated;

$R^{10}$ and $R^{12}$, independently of each other, are constituted of $C_{1-5}$ alkyl, $C_3$-$C_5$ cycloalkyl, $C_{2-5}$ alkenyl, $C_{2-5}$ alkinyl, $C_{1-5}$ alkoxy, $C_{1-5}$ alkylcarbonyl, $C_{1-5}$ alkoxycarbonyl, $C_{1-5}$ alkylthio, $C_{1-5}$ alkylamino, $C_{1-5}$ alkylsulfinyl, $C_{1-5}$ alkylsulfonyl, $C_{1-5}$ alkylamino-$C_{1-5}$ alkyl, $C_{1-5}$ alkylthio-$C_{1-5}$ alkyl or $C_{1-5}$ alkoxy-$C_{1-5}$ alkyl;

$Q^4$ and $Q^6$, independently of each other, are hydrogen, hydroxy, formyl, carboxy, halogen, mercapto, sulfonyl, amino or amido.

Particular preference for producing an analgesic is given to those azaspiro compounds which in the formalin test, described in Example #7, bring about a mean deviation of the pain reaction of at least −40% and preferably at least −50% or −60% in at least one and preferably in at least two of the test periods (20-25', 30-35', 40-45' after the administration of formalin).

For the purpose of this patent application, the term "mean deviation of the pain reaction" refers to a relative deviation that is obtained when the average time of pain reaction of 10 animals treated with active agents in a test series as described in implementation Example #7 is compared, over a defined period (20-25', 30-35' or 40-45' after formalin injection), with the average time of the pain reaction of 10 control animals treated with an excipient. A reduction in the pain reaction is expressed in negative percentage figures.

The medications containing the azaspiro compounds per this invention can essentially be used for treating various types of pain such as migraine, skeletal and muscle pain, etc. However, analgesics containing these novel azaspiro compounds lend themselves particularly well to the treatment of chronic, chronic-phlogistic and/or neuropathic pain.

Neuropathic pain is a complex syndrome often encountered as a consequence of injuries, infections, metabolic disorders and degenerative diseases of the nervous system. Examples of a neuropathic pain syndrome include pseudesthesia, postherpetic neuralgia following herpes zoster, painful diabetic neuropathy, complex regional pain syndromes, various types of cancer-related pain, neuropathic pain in connection with multiple sclerosis or with injuries to a major neuroplexus, to the spinal cord or to the brainstem.

As is evident from FIG. 1, it is especially the novel azaspiro compounds per formula IIa that lend themselves well to the treatment of chronic, chronic-phlogistic and/or neuropathic pain.

Accordingly, one object of this invention is the use of an azaspiro compound per general formula IIa Formula IIa

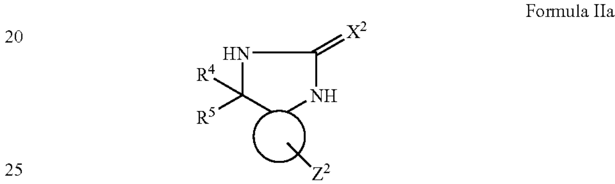

where the nature of $X^2$, $R^4$, $R^5$ and $Z^2$ is as indicated above, or of a tautomer and/or pharmaceutically acceptable salt of this compound, for producing a medication for the treatment of pain and especially chronic, chronic-phlogistic and/or neuropathic pain.

For producing medications serving to treat pain and especially chronic, chronic-phlogistic and/or neuropathic pain, preferential use is made of azaspiro compounds per general formula IIa in which the ring $Z^2$ of the azaspiro compound is an unsubstituted ring and/or a saturated ring with 5, 6 or 7 ring-forming atoms including the azaspiro atom.

For producing medications serving to treat and alleviate pain, particular preference is given to the use of azaspiro compounds per general formula IIa in which the ring $Z^2$ is a hydrocarbon ring and ideally a saturated, unsubstituted hydrocarbon ring, constituted in particular of cyclopentane, cyclohexane or cycloheptane.

In another preferred implementation of the invention, the analgesic is produced with an azaspiro compound per general formula IIa in which both the substituents $R^4$ and $R^5$ are hydrogen or jointly form an oxo or thioxo group.

In another preferred implementation of the invention, $X^2$ is oxygen or sulfur.

Especially preferred are azaspiro compounds per formula IIa selected from among 1,3-diaza-spiro[4.5]decane-2.4-dion 1,3-diaza-spiro[4.5]decane-2.4-dithion 1,3-diaza-spiro[4.5]decane-2-on 1,3-diaza-spiro[4.5]decane-2-thion and their pharmaceutically acceptable salts for producing a medication serving to treat pain, especially chronic, chronic-phlogistic and/or neuropathic pain.

In another implementation of the invention the analgesic is produced through the use of an azaspiro compound per general formula IIb Formula IIb

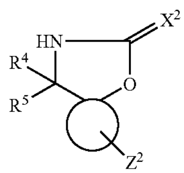

where the nature of $R^4$, $R^5$, $X^2$ and $Z^2$ is as indicated above, or of a tautomer and/or pharmaceutically acceptable salt of this compound.

In producing medications for the treatment of pain, especially chronic, chronic-phlogistic and/or neuropathic pain, preference is given to the use of azaspiro compounds per general formula IIb in which the ring $Z^2$ of the azaspiro compound is an unsubstituted ring and/or a saturated ring with 5, 6 or 7 ring-forming atoms including the azaspiro atom.

Especially preferred in producing medications for the treatment and alleviation of pain are azaspiro compounds per general formula IIb in which the ring $Z^2$ is a hydrocarbon ring and ideally a saturated, unsubstituted hydrocarbon ring consisting in particular of cyclohexane.

In another preferred implementation of the invention, the analgesic is produced with an azaspiro compound per general formula IIb in which both substituents $R^4$ and $R^5$ are hydrogen or jointly form an oxo or thioxo group.

In another preferred implementation of the invention, $X^2$ is oxygen or sulfur.

Azaspiro compounds that are particularly suitable for producing the analgesic include for instance 1-oxa-3-aza-spiro[4.5]decane-2-on or 1-oxa-3-aza-spiro[4.5]decane-2-thion.

Finally, this invention encompasses new azaspiro compounds selected from among 1-oxa-3-aza-spiro[4.5]decane-2-on 1-oxa-3-aza-spiro[4.5]decane-2-thion 1-3-diaza-spiro[4.5]decane-2-on 1-3-diaza-spiro[4.5]decane-2-thion and 1-3-diaza-spiro[4.5]decane-2.4-dithion as well as methods for their production.

The following examples will explain this invention in more detail.

1. Production of 1-oxa-3-aza-spiro[4.5]decane-2-on 0.65 g (5.0 mmol) of 1-(aminomethyl)-cyclohexanol, 1.2 g (5.5 mmol) di-tert.-butyldicarbonate ($(Boc)_2O$) and 0.611 g 4-dimethylaminopyridine were dissolved in 50 ml acetonitrile and agitated overnight at room temperature. The mixture was then fully turned over, the residue was dissolved in 20 ml acetic acid and again turned over. The residue was taken up in 25 ml 1 M hydrochloric acid and extracted with 50 ml toluene.

After removal of the toluene and recrystallization from methyl-tert. butylether the product precipitated in the form of colorless acicular crystals.

The yield was 15.5% of theoretical.

NMR ($CDCl_3$): 159.97; 82.82; 51,32; 36.36; 24.64; 22.23

2. Production of 1-oxa-3-aza-spiro[4.5]decane-2-thion 4.3 g (33.3 mmol) of 1-(aminomethyl)-cyclohexanol and 8.16 g (41.2 mmol) N,N'-thiocarbonyldiimidazol (tech. 90-%) were dissolved in 250 ml dichloromethane and allowed to sit for 1 hour at room temperature. The preparation was extracted with 250 ml 1 M hydrochloric acid and the organic phase was fully turned over.

The total residue was recrystallized from 40 ml ethyl acetate. The product crystallized at room temperature. To complete crystallization, the preparation was allowed to sit overnight at −25° C. The supernatant was siphoned off, the crystals were rinsed with 5 ml methyl-tert.-butylether and dried at room temperature in a vacuum drying chamber.

The yield was 4.4 g (77.2% of theoretical)

The melting point was determined at 152.0° C.

NMR ($CDCl_3$): 188.35; 90.64; 54.07; 35.50;24.35; 22.29.

3. Production of 1.3-diaza-spiro[4.5]decane-2.4-dion

A solution of 4.9 g (5.15 ml, 50 mmol) cyclohexanone, 4.88 g (75 mmol) potassium cyanide and 14.4 g (150 mmol) ammonium carbonate in 100 ml aqueous 50% ethanol was agitated in an oil bath at 65° C. for 24 hours. The mixture was then diluted with 300 ml water and refluxed for 15 minutes. Subsequently the mixture was cooled to 0% ° C. and poured over 300 ml cold 6N hydrochloric acid. The precipitate was filtered out, rinsed in cold water and dried in the vacuum drying chamber.

The yield was 7.23 g (86%).

Thin-layer chromatography (silica gel 60, n-heptane/ethyl acetate 1/1; development with diluted $KMnO_4$ solution) produced a uniform product with an $R_f$ value of 0.24.

The melting point was determined at 218.2° C.

NMR ($CD_3OD$): 180.92; 158.87; 64.38; 34.58; 25.80; 22,45.

4. Production of 1.3-diaza-spiro[4.5]decane-2.4-dithion

A solution of 1 g (6.0 mmol) 1,3-diaza-spiro[4.5]decane-2,4-dion (ref. Example #3; barely soluble) in 50 ml toluene was mixed in a nitrogen atmosphere with 2.47 g Lawson reagent (2,4-bis-(4-methoxyphenyl)-2,4-dithioxo-1,3,2,4-dithiadiphosphetane) and refluxed in a nitrogen atmosphere (115° C.) for 26 hours. The solution was cooled to room temperature and filtered through spun glass wool. The filtrate was concentrated and purified through flash chromatography (heptane/ethyl acetate 9:1).

The yield was 781 mg (65%).

Thin-layer chromatography (silica gel 60, n-heptane/ethyl acetate 1/1; development with alkaline $KMnO_4$ solution) produced a uniform product with an $R_f$ value of 0.94 (educt: 0.31).

The melting point was determined at 271° C.

NMR (DMSO-d6): 212.19; 180.45; 77.41; 36.97; 24.68; 21.15.

5. Production of 1.3-diaza-spiro[4.5]decane-2-on

Added to 1.6 g (9.5 mmol) of 1.3-diaza-spiro[4.5]decane-2.4-dion (ref. Example #3) in 20 ml diethyl ether was 20 ml of a 1 M solution of lithium aluminum hydride in diethyl ether at 0° C. The mixture was agitated for 4 hours at room temperature. The mixture was subsequently cooled to 0° C. and mixed with 3 ml $H_2O$, 2 ml 15% soda lye and 5 ml $H_2O$. The solution was then mixed with 80 ml of hot ethanol and filtered. The filtrate was turned over, taken up in ethyl acetate and filtered again. Concentrating the filtrate produced 1.2 g of a colorless crystalline product in an 82% yield.

Thin-layer chromatography (silica gel 60, n-heptane/ethyl acetate 1/1; development with alkaline $KMnO_4$ solution) produced a uniform product with an $R_f$ value of 0.03.

The melting point was determined at 221° C.

NMR ($CDCl_3$): 163.12; 57.67; 51.96; 37.58; 25.03; 22.65.

6. Production of 1.3-diaza-spiro[4.5]decane-2-thion

This compound can be produced by first generating 1.3-diaza-spiro[4.5]decane-2-on as described in Example #5, then converting it with the Lawson reagent as described in Example #4.

1. In-vivo Test for Determining the Analgesic Effectiveness of the Azaspiro Compounds The test was conducted as described by Wheeler-Aceto (Psychopharmacology 104, 1991, 35).

NMRI mice having a weight of 20-25 g were kept under controlled conditions (22±2° C., 40-70% relative humidity). 25 μl of a 5% formocarbonyl solution was injected in the hind leg and the leg-licking frequency was then clocked for 5 minutes each at defined intervals (20, 30, 40 minutes).

First, the highest possible non-toxic concentration of the respective test substances that could be used was determined by an IRWIN test (Irwin, Psychopharmacologia 13, 1968, 222).

Next, for the formalin test, the test substances were dissolved in a physiological salt solution with 0.5% sodium carboxymethyl cellulose and were each measured in 1-3 dosages that had been applied intraperitoneally 10 minutes before administration of formalin. The comparative reference value was provided by a control excipient (10 ml/kg).

The test was performed in blind fashion on 10 mice per test series. The evaluation was based on a comparison of the treated animals with control excipients at three different times. To that end, a pain-reaction mean value per time period was established for the 10 animals of a test series followed by the determination of the relative deviation of the animals treated with the effective agent from the control animals in each of the three different periods. Accordingly, an average 50% reduction of the pain reaction for the treated animals is obtained when in a defined period (e.g. 30-35' after the formalin injection) the leg-licking duration (averaged over the 10 test animals) is reduced by 50% compared to the untreated animals. The statistical significance was determined using the Mann-Whitney U-test.

All documents mentioned herein are incorporated herein by reference in their entirety.

The invention claimed is:

1. A method for the treatment of pain in a subject in need thereof, comprising administering to the subject a compound of general Formula II:

Formula II

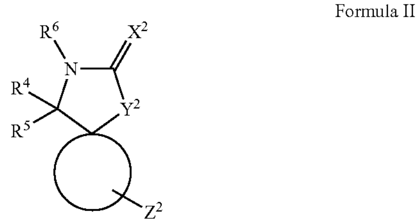

where $y^2$ represents S, NH or O;

$X^2$ represents S;

$R^4$ and $R^5$ independently of each other represent hydrogen, hydroxy, formyl, carboxy, halogen, mercapto, sulfonyl, amino, amido or a —$R^{10}$ optionally substituted with a $Q^4$ group or jointly form an oxo or thioxo group;

$R^6$ is hydrogen, hydroxy, amino or a —$R^{11}$ optionally substituted with a $Q^5$ group; $Z^2$ is a 4-10 membered saturated or unsaturated hydrocarbon ring optionally substituted at any ring atom with one or several substituents independently selected from hydrogen, hydroxy, formyl, carboxy, halogen, mercapto, sulfonyl, amino, amido or a—$R^{12}$ optionally substituted with a $Q^6$ group;

$R^{10}$, $R^{11}$ and $R^{12}$, independently of one another, represent $C_{1-5}$ alkyl, $C_3$-$C_6$ cycloalkyl, $C_{2-5}$ alkenyl, $C_{2-5}$ alkinyl, $C_{1-5}$ alkoxy, $C_{1-5}$ alkylcarbonyl, $C_{1-5}$ alkoxycarbonyl, $C_{1-5}$ alkylthio, $C_{1-5}$ alkylamino, $C_{1-5}$ s alkylsulfinyl, $C_{1-5}$ alkylsulfonyl, $C_{1-5}$ alkylamino-$C_{1-5}$ alkyl, $C_{1-5}$ alkylthio-$C_{1-5}$ alkyl or $C_{1-5}$ alkoxy-$C_{1-5}$ alkyl;

$Q^4$, $Q^5$ and $Q^6$, independently of one another, are hydrogen, hydroxy, formyl, carboxy, halogen, mercapto, sulfonyl, amino or amido, or free base, tautomer, enantiomer, racemate thereof, or a pharmaceutically acceptable salt of any of the foregoing.

2. The method of claim 1, with $R^6$ being hydrogen.

3. The method of claim 1, where $R^6$ is hydrogen and $Y^2$ is NH.

4. The method of claim 1, where $R^6$ is hydrogen and $Y^2$ is oxygen.

5. The method as in claim 1, where $Z^2$ is a 5-, 6- or 7-member ring.

6. The method as in claim 1, where $Z^2$ is saturated.

7. The method as in claim 1, where $Z^2$ is unsubstituted.

8. The method as in claim 1, where $Z^2$ is a hydrocarbon ring.

9. The method as in claim 1, where $Z^2$ is cyclopentane, cyclohexane or cycloheptane.

10. The method as in claim 1, where both $R^4$ and $R^5$ are hydrogen or jointly form an oxo or thioxo group.

11. The method as in claim 10, where $R^4$ and $R^5$ jointly form a thioxo group, $Z^2$ is cyclohexane, and $R^6$ is hydrogen.

12. The method of claim 1, whereby the compound is selected from:

1,3-diaza-spiro[4.5]decane-2,4-dithione;

1,3-diaza-spiro[4.5]decane-2-thione; or 1-oxa-3-aza-spiro[4.5]decane-2-thione.

13. The method of claim 1 wherein both $R^4$ and $R^5$form an thioxo group, and $Y^2$ is NH.

14. The method as in claim 1, where the pain treated is chronic pain.

15. The method of claim 1, where the pain treated is chronic-inflammatory pain.

16. The method of claim 1, where the pain treated is acute chronic pain.

17. The method of claim 1, where the pain treated is neuropathic pain.

18. The method as in claim 12, where the pain treated is chronic pain.

19. The method of claim 12, where the pain treated is chronic-inflammatory pain.

20. The method of claim 12, where the pain treated is acute chronic pain.

21. The method of claim 12, where the pain treated is neuropathic pain.

22. The method of claim 11, wherein $Y^2$ is NH.

23. The method of claim 11, wherein the subject is a mammal.

24. The method of claim 11, wherein the subject is a human.

25. The method of claim 11, wherein an effective amount of the compound is administered to the subject.

26. The method as in claim 3, where $Z^2$ is a 5-, 6- or 7-member ring.

27. The method as in claim 3, where $Z^2$ is saturated.

28. The method as in claim 3, where $Z^2$ is unsubstituted.

29. The method as in claim 3, where $Z^2$ is a hydrocarbon ring.

30. The method as in claim 3, where $Z^2$ is cyclopentane, cyclohexane or cycloheptane.

31. The method as in claim 3, where both $R^4$ and $R^5$ are hydrogen or jointly form an oxo or thioxo group.

32. The method as in claim 31, where $R^4$ and $R^5$ jointly form a thioxo group, $Z^2$ is cyclohexane, and $R^6$ is hydrogen.

33. The method of claim 3, whereby the compound is selected from:

1,3-diaza-spiro[4.5]decane-2,4-dithione; or 1,3-diaza-spiro[4.5]decane-2-thione.

34. The method of claim 33, where the compound is 1,3-diaza-spiro[4.5]decane-2,4-dithione.

35. The method of claim 12, wherein the subject is a mammal.

36. The method of claim 12, wherein the subject is a human.

37. The method of claim 12, wherein an effective amount of the compound is administered to the subject.

* * * * *